United States Patent
James

[11] Patent Number: 5,221,202
[45] Date of Patent: Jun. 22, 1993

[54] PACKAGING AND ADHESIVE FOR PREDISPENSED ORTHODONTIC BRACKETS

[76] Inventor: Jack L. James, P.O. Box 6081, San Diego, Calif. 92166

[21] Appl. No.: 870,796

[22] Filed: Apr. 17, 1992

Related U.S. Application Data

[63] Continuation of Ser. No. 684,660, Apr. 12, 1991, abandoned.

[51] Int. Cl.$^5$ .................. A61C 3/00; A61B 19/02; B65D 83/10
[52] U.S. Cl. .................. 433/9; 206/63.5; 206/369
[58] Field of Search .................. 433/8, 9; 206/63.5, 206/83, 368, 369

[56] References Cited

U.S. PATENT DOCUMENTS

| | | | |
|---|---|---|---|
| 2,148,721 | 2/1939 | Avstreih | 206/369 |
| 3,751,399 | 8/1973 | Lee, Jr. | |
| 3,792,531 | 2/1974 | Rossi | |
| 4,094,068 | 6/1978 | Schinhammer | 433/9 |
| 4,163,004 | 7/1979 | Erikson et al. | |
| 4,204,325 | 5/1980 | Kaelble | 433/9 |
| 4,220,582 | 9/1980 | Orlowski et al. | |
| 4,340,529 | 7/1982 | Lee, Jr. et al. | |
| 4,820,545 | 4/1989 | Negrych | |
| 4,826,430 | 5/1989 | Chen et al. | |
| 4,948,367 | 8/1990 | Haas | 433/9 |
| 4,978,007 | 12/1990 | Jacobs et al. | 206/368 X |
| 4,979,611 | 12/1990 | Bolliger et al. | 206/83 |
| 4,991,759 | 2/1991 | Scharf | 206/368 X |
| 5,015,180 | 5/1991 | Randklev | 433/9 |

Primary Examiner—John J. Wilson
Assistant Examiner—Nicholas D. Lucchesi
Attorney, Agent, or Firm—Lyon & Lyon

[57] ABSTRACT

Packaging for orthodontic brackets having a pre-dispensed adhesive. The packaging comprises light opaque compartments, each compartment sized and dimensioned to contain a bracket, and having a reservoir such that adhesive applied to a portion of the bracket will remain in contact with that portion of the bracket, and will not be distributed over other portions of the bracket. Also, a formulation of adhesive adapted for pre-dispensing to orthodontic brackets, comprising Bis/GMA, EBADMA, and at least one polymerizing agent.

10 Claims, 1 Drawing Sheet

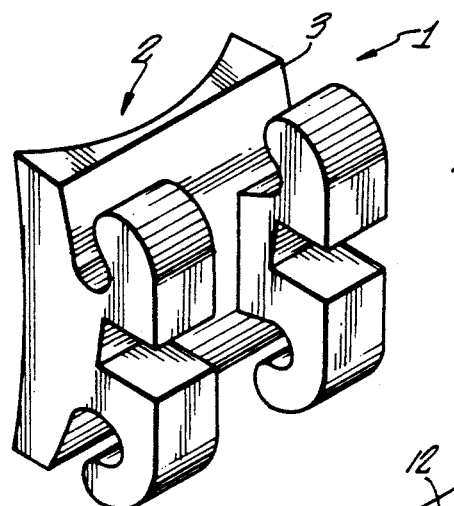
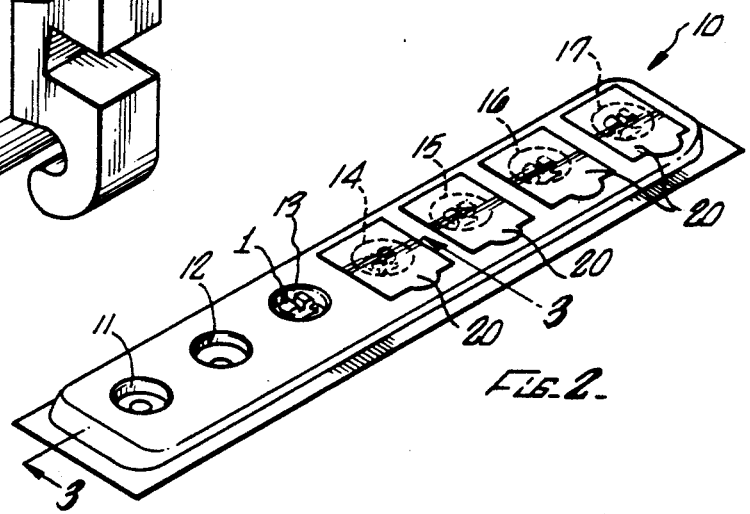
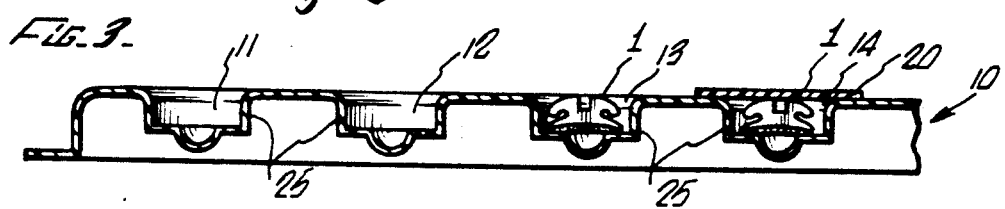
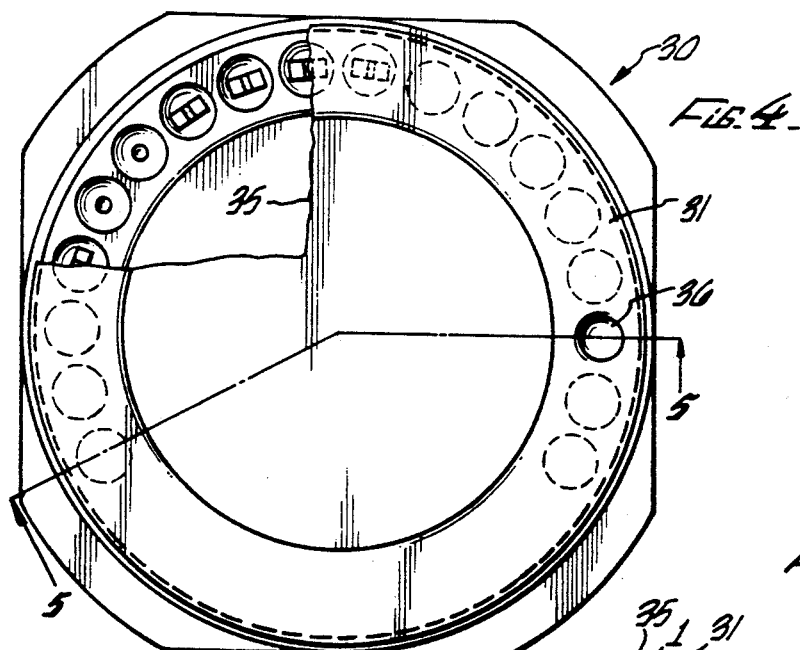
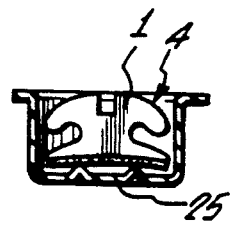
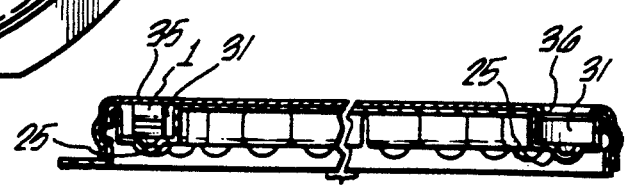

PACKAGING AND ADHESIVE FOR PREDISPENSED ORTHODONTIC BRACKETS

This is a continuation of co-pending application Ser. No. 07/684,660, filed on Apr. 12, 1991 now abandoned and which designated the U.S.

BACKGROUND OF THE INVENTION

The present invention relates to the field of orthodontics, and more particularly to the field of orthodontic supplies including brackets and adhesives.

Orthodontists move patients' teeth into desired positions by applying gentle, but constant force to the teeth. As much as two years of gentle force may be required to coax teeth into their proper positions. At present, the process may involve preparation of the teeth through application of a chemical etching agent such as phosphoric acid. Small metal, plastic or ceramic brackets are then bonded to the surface of the prepared teeth using a dental adhesive. The brackets are linked together with wire or other linkage such that forces can be transmitted in a controlled manner to the teeth.

Different adhesives have been used over the years. In the early 1960s, a first generation of adhesives used for orthodontic brackets was developed which relied upon straight epoxy resins. These adhesives proved generally unsatisfactory because of their slow set-up times of up to 30 minutes. In the late 1960's and 1970's, a second generation of adhesives came on the market. These adhesives relied upon a dimethylacrylate monomer, (Bisphenol A Diglycidyl Methacrylate, known in the art as Bis/GMA), which was cut with low viscosity diacrylate diluents such as Triethylene Glycol Dimethylacrylate (known in the art as TEGDM or TEGDMA). In the late 1970's a third generation of orthodontic adhesives known as "honeymoon" adhesives became available which utilized high molecular weight polymeric fillers and blends of mono- and dimethylacrylates. These adhesives require the orthodontist to brush a primer on the surface of the bracket and on the tooth. A higher viscosity paste is then placed on the bracket, and the bracket placed on the tooth. A fourth generation of adhesives were light curable and provided convenience of simplified application and reduced application times. Light curing enables the practitioner to take as long as needed to position the bracket, and then rapidly fix it in place with a short exposure to UV, infrared, visible or some other wavelength or wavelengths of light.

Presently available light cured systems are generally based on Bowen's resin, which comprises Bis/GMA, TEGDMA, and inorganic filler particles, and was disclosed in Erickson et al, U.S. Pat. No. 4,163,004, issued Jul. 31, 1979. One example of such systems is TRANS-BOND (TM) sold by MINNESOTA MINING AND MANUFACTURING CO. (TM). Another example is LIGHT BOND (TM) manufactured by RELIANCE ORTHODONTICS (TM). In such systems, a practitioner typically prepares an adhesive on an "as needed" basis. The prepared adhesive is applied to a bracket, and the bracket-with-adhesive is positioned on an etched portion of the tooth. The adhesive is cured with the application of visible or UV light. The adhesives and brackets are purchased and inventoried separately. Several differently shaped and sized brackets are used to accommodate different teeth and orthodontic purposes. Typically, the brackets are constructed from various materials, including metal, ceramic, plastic, and combinations of these materials.

Although the above-described bonding system is an improvement over methods used thirty years ago, several problems remain. One problem is that the practitioner must typically prepare the adhesive by mixing two or more substances together. Since the adhesives may be workable for only a relatively short period of time, the mixing process may need to be repeated many times in a given day, resulting in considerable inconvenience. Also, since the exact proportions of the substances in the adhesive may vary from mixture to mixture, adhesive mixtures with sub-optimal properties may be produced. Still another problem is that the brackets are relatively small, and the process of dabbing adhesive onto the brackets may be inconvenient and may result in spattering of adhesive onto undesired areas of the bracket or the skin. Still another problem is that the bonding strength of currently available adhesives may be excessive when used with ceramic brackets. Still another problem is that the Bowen's resin may tend to become stained or discolored during use.

SUMMARY OF THE INVENTION

The present invention resolves the above-mentioned problems by pre-dispensing orthodontic brackets along with a special, premixed adhesive. The packaging is designed to accommodate both bracket and adhesive in such relation that the adhesive remains affixed to a certain portion of the bracket, and does not contact any other portions. The adhesive is specially formulated to be stable over a relatively long period of time, and over a relatively wide range of temperatures, while still maintaining the desirable characteristics of other modern orthodontic adhesives.

According to an exemplary embodiment of the invention, the packaging comprises a container having a multiplicity of compartments. Each compartment is large enough to contain a single orthodontic bracket, but small enough to prevent the bracket from moving around excessively within the compartment. Each compartment has a bottom which is shaped to act as a reservoir for the adhesive. Each compartment also has an opening which may be covered by a removable tab. The container is fabricated from PVC plastic which is non-reactive to the adhesive, and which acts as a barrier to prevent light from striking the adhesive. The adhesive is formulated from Bis/GMA and EBADMA (Ethoxylated Bisphenol A Dimethylacrylate).

Accordingly, it is an object and advantage of the present invention to supply dental practitioners with orthodontic brackets to which an adhesive has been pre-dispensed.

It is a further object and advantage of the present invention to obviate the need for dental practitioners to prepare a dental adhesive by mixing substrates in the office;

It is a further object and advantage of the present invention to reduce the inconvenience by dental practitioners in preparing dental adhesive and applying the adhesive to orthodontic brackets in their offices.

It is a further object and advantage of the present invention to control the proportions of components in dental adhesives by providing orthodontic brackets to dental practitioners with dispensed adhesive.

It is a further object and advantage of the present invention to provide dental practitioners with a premixed light sensitive dental adhesive, which can be packaged in combination with dental brackets.

It is a further object and advantage of the present invention to provide dental practitioners with a dental adhesive having superior stain resistance than the common Bowen's resin.

BRIEF DESCRIPTION OF THE DRAWINGS

These and other objects of the present invention will become better understood through a consideration of the following description taken in conjunction with the drawings in which:

FIG. 1 is a perspective view of a dental bracket.

FIG. 2 is a perspective view of a bracket container having seven compartments.

FIG. 3 is a cross-sectional view of the bracket container of FIG. 2, taken across line 3—3.

FIG. 4 is a top view of a circular bracket container showing a partial cutaway.

FIG. 5 is a cross-section of the bracket container of FIG. 4, taken along line 5—5.

FIG. 6 is a cross-sectional view of a compartment.

DETAILED DESCRIPTION OF THE INVENTION

Turning now to the drawings, FIG. 1 depicts a bracket 1 having a bonding surface 2 for bonding to a tooth (not shown), and a linkage surface 3 for receiving linkages (not shown). Since the present application is intended to comprehend all types of dental brackets, including metal, ceramic and plastic brackets of different manufacturers, the bracket 1 is intended to be generic. The bracket 1 need not be shaped as shown, and the surfaces 2, 3 need not be shaped or positioned as shown.

In FIG. 2, a linear container 10 comprises seven separate compartments 11-17 extending from a common surface 18. The specific number of compartments is not critical, and a greater or fewer number than seven compartments is possible. In the presently preferred embodiment, each of the compartments 11-17 contain a single bracket 1. Depending on the intent of the manufacturer, the brackets contained within a multi-compartment container may either be identical or different from one another. Since the preferred adhesive is light cured and may react with certain materials, the container is preferably constructed of pigmented polyvinyl chloride, PVC, which is both relatively impermeable to light, and is relatively inert to the preferred adhesive. One skilled in the art will recognize that the container can also be constructed of other materials, including without limitation properly pigmented polymers, metals, ceramics or combinations thereof.

Each bracket 1 is held within its respective compartment 11-17 by a removably affixed tab 20. In the preferred embodiment, each tab 20 is glued to the common surface 18 with pressure sensitive adhesive, permitting the tab 20 to be pulled off by the dental practitioner. Several alternative mechanisms of attachment of the tab will be apparent to those skilled in the art. For illustration purposes only, the tabs 20 and brackets 1 have been removed from compartments 11-12, the tab 20 has been removed from compartment 13 to expose a bracket 1.

In FIG. 3, each compartment 11-14 has a reservoir 25 within which is placed an adhesive (not shown). The amount of adhesive, and the viscosity of the adhesive are such that as long as the bracket lies within the compartment, the adhesive will contact the first surface 2 of the bracket 1, and will not contact other portions of the bracket 1. There are numerous reservoir shapes which are acceptable. By way of example, and without limitation, the reservoir 25 may be hemispherical as in FIG. 3; it may have elevated sides as shown in the compartment 4 of FIG. 6, or it may be "V" shaped or "U" shaped (not shown). The reservoir 25 may also comprise a uneven or dimpled surface (not shown). Also, in FIG. 6, the adhesive 40 is shown contacting the reservoir 25 and the bracket 1.

FIG. 4 shows an alternative embodiment of bracket dispenser 30 in circular form. In this embodiment, each compartment 31 again contains a single bracket 1, but the instead of tabs 20, the brackets 1 are held within the compartments 31 by a rotating cover 35 which has been cut away for purposes of illustration. The cover 35 has a single opening 36 which can be sequentially positioned over each compartment 31 to access the enclosed bracket 1.

FIG. 5 is a cross-section taken along line 5—5 in FIG. 4. The opening 36 in the cover 35 overlies one of the compartments 31. For illustration purposes, the bracket 1 in that compartment 31 has been removed.

The packaging portion of the present invention should now be apparent from FIGS. 1-5. To summarize, a container is constructed to have one or more compartments, generally each compartment containing a bracket. Adhesive is pre-dispensed onto each of the brackets. The pre-dispensing can occur according to numerous steps, such as by first placing adhesive into the reservoir the compartment and then placing the bracket within the compartment such that the bracket contacts the adhesive, or alternatively by placing the adhesive onto the bracket and then placing the bracket-with-adhesive into the compartment. A reservoir within each compartment assists in keeping a sufficient quantity of adhesive in contact with the bracket, while assisting in preventing adhesive from moving freely around the compartment. A tab, cover, or other means keeps each bracket within its compartment until needed.

Turning to the particular composition of the adhesive, it will be apparent that any pre-dispensed adhesive must at least meet the requirements of standard dental adhesives. It must be nontoxic, and retain satisfactory strength, color stability, stain resistance and workability while in storage for up to a year or more. Satisfactory strength is defined as 1000 psi to 3000 psi. Satisfactory workability is defined as a setting time between 20 and 60 seconds, and a consistency that is fluid enough to conform to the surface of the tooth (wetting out), but not so fluid that the bracket will slide down the tooth before it cures. The adhesive must also have several characteristics which are not usually required of standard dental adhesives. The dispensed adhesive must have sufficiently high viscosity to present free movement of the adhesive within the compartments, and yet sufficiently low viscosity so that it can be conveniently applied to the brackets during packaging and properly "wet out" the surface of the tooth during application. The pre-dispensed adhesive must have a long shelf life. Experimentation has shown that previously known adhesives may not be satisfactory for pre-dispensing onto brackets. The adhesive used in the preferred embodiment comprises the following:

60 parts Bis/GMA
40 parts EBADMA
7 parts fumed silica
0.11 parts Camphorquinone 0.11 parts EBAD As noted above, Bis/GMA is the acronym for a chemical known as Bisphenol A Diglycidyl Methacrylate. It is commercially available as NUPOL 046-4005 from Freeman Chemical Corp. of Port Washington, Wis. The chemical structure of Bis/GMA is

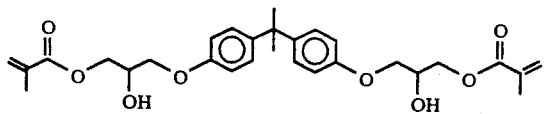

EBADMA is the acronym for Ethoxylated Bisphenol A Dimethylacrylate. It is available from Sartomer Company of West Chester, Pa. resin 190 348. The chemical structure of EBADMA is

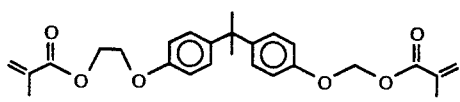

Camphorquinone is a chemical added to the resin mixture as a photo-initiator. It is available from Hampford Research, Inc. of Stratford, Conn. The chemical structure of camphorquinone is

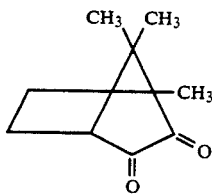

The fumed silica is added to thicken the viscosity of the adhesive. It is available from Degussa Corp. as Aerosil R974 and has an average particle size of 12 nanometers. The chemical structure of fumed silica is

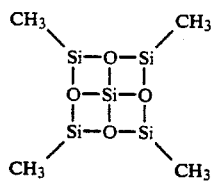

EBAD is the acronym for Ethyl-4-(Dimethylamino) Benzoate. It can also be obtained from Hampford Research, Inc. of Stratford, Conn. It works as an electron transfer agent in conjunction with the Camphorquinone to initiate polymerization. Its structure is

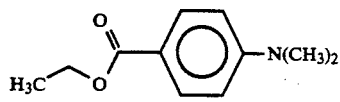

Other optical ingredients such as pigments, opacifiers, dyes, ultraviolet light absorbers, polymerization inhibitors may be added to the formula to enhance various properties. Also alternative polymerization initiators, electron transfer agents and thickeners may also be used.

In mixing the adhesive, one should work in a darkened environment, avoiding strongly intense light especially in the ultraviolet and violet and blue ranges of the spectrum. The adhesive is mixed in the following steps: (1) Add the EBADMA to an opaque mixing vessel equipped for mechanical stirring; (2) Add the EBAD and camphorquinone to the vessel and stir until both compounds are dissolved; (3) Add the Bis/GMA to the vessel and stir until homogeneous; and (4) Add the finely divided silica and stir until a uniform consistency has been reached.

The inventor conducted several experiments which support the efficacy of the preferred adhesive. In one experiment, sample brackets with pre-dispensed adhesive in accordance with the disclosure in this application were tested after storage for one week, one month, two month, six month and one year periods. GENIE ORTHODONTIC ADHESIVE ™ manufactured by LEE PHARMACEUTICALS ™ was used as a control. Visual observation of the uncured samples just prior to bonding at each time interval demonstrated no discoloration, thickening or evidence of polymerization. Visually the samples were unchanged in storage. Shear adhesion tests performed at each time interval also indicated good long-term stability. The one year test is still in process.

TABLE 1

| | Shear Adhesion (lbs) | |
| --- | --- | --- |
| Time | Pre-Dispensed Brackets | GENIE (TM) |
| Baseline | 32.1 +/− 2.3 (2050 psi) | 42.1 +/− 4.6 (2690 psi) |
| 7 Days | 36.0 +/− 2.8 (2300 psi) | 46.7 +/− 6.4 (3000 psi) |
| 30 Days | 30.9 +/− 3.3 (1980 psi) | 43.4 +/− 5.9 (2780 psi) |
| 60 Days | 28.4 +/− 6.3 (1820 psi) | 38.7 +/− 3.8 2480 PSI |
| 180 Days | 30.2 +/− 4.6 (1930 psi) | 39.5 +/− 4.3 (2530 PSI) |

In another experiment, samples were frozen at approximately minus 28 degrees Celsius for seven days. Visual examination of the frozen samples indicated no visual degradation. Shear adhesion tests performed on the frozen samples also indicated good stability under freezing temperatures.

TABLE 2

| | Shear Adhesion (lbs) | |
| --- | --- | --- |
| Sample | Baseline | 7 Days Freezing |
| pre-dispensed brackets | 36.0 +/− 4.8 (2300 psi) | 30.0 +/− 3.2 (1920 psi) |

In another experiment, samples were heated to 65 degrees celsius and 100% humidity for seven days. Shear adhesion tests performed on the frozen samples also indicated good stability

TABLE 3

| | Shear Adhesion (lbs) | |
| --- | --- | --- |
| Sample | Baseline | 7 Days of Heat |
| pre-dispensed brackets | 36.6 +/− 4.8 (2300 psi) | 31.2 +/− 3.9 (1920 psi) |

In another experiment the inventor tested bracket flotation. When a dental practitioner places a bracket on a tooth, the consistency of the unpolymerized bracket adhesive must hold the bracket in place until polymerization can firmly affix the position of the bracket. If excess bracket flotation occurs, the bracket will not remain in position. To test the degree of bracket flotation, a clean plate was mounted in a vertical position in an oven at 37 degrees celsius. A thin, straight, horizontal line had previously been scribed into the surface of the glass. After the glass had been allowed ample time to reach 37 degrees celsius, ten brackets having the preferred adhesive were pressed into position on the scribed line. The brackets were allowed to sit for a period of five minutes and were observed for evidence of sliding down the surface of the glass. This test was intended to simulate the warm vertical surface of an orthodontic patient's tooth. The results were that after five minutes, all of the brackets had remained immobile on the glass.

In another experiment the inventor tested pre-dispensed brackets on bovine teeth which had previously been etched with phosphoric acid. This test was intended to provide a close correlation to actual usage on patients. Upon debonding, the brackets separated from the teeth at the adhesive enamel interface under a shear adhesion force of 35.5 lbs $+/-2.7$ lbs. The fact that all of the samples debonded without fracturing the brackets and without damaging tooth enamel was taken as an indication that the debonding strength is not too high.

In another experiment, the inventor experimented with bonding strength of the formulations having different ratios of Bis/GMA to EBADMA. The following ratios were tested:

TABLE 4

| Formulations Used To Test Bonding Strength |
| --- |
| 1. 90 parts Bis/GMA to 10 parts EBADMA; |
| 2. 80 parts Bis/GMA to 20 parts EBADMA; |
| 3. 60 parts Bis/GMA to 40 parts EBADMA; |
| 4. 40 parts Bis/GMA to 60 parts EBADMA; |
| 5. 20 parts Bis/GMA to 80 parts EBADMA; |
| 6. 00 parts Bis/GMA to 100 parts EBADMA. |

To each of these mixture was added 0.1 parts per hundred by weight of Camphorquinone and Ethyl-4-(Dimethylamino) Benzoate. These components made the resin mixtures capable of being polymerized with visible light. The mixtures were heated to 40 degrees Celsius and stirred until all the components had dissolved. Ten polycrystaline alumina orthodontic brackets with a flat square base, having a surface area of 0.016 square inches were bonded to acrylic studs using the prepared resin mixtures. Ten brackets for each resin mix were utilized. A 110 volt, 150 watt, projector lamp at a distance of six inches was exposed to each bracket for a period of 10 seconds to facilitate bonding to the acrylic studs. The samples were aged 24 hours in water and then tested for shear adhesion. The shear adhesion results are listed below:

TABLE 5

Results Of Different Formulations On Bonding Strength

| SAMPLE | SHEAR ADHESION |
| --- | --- |
| 1. 90 parts Bis/GMA to 10 parts EBADMA | 28.2 +/− 4.1 lbs. |
| 2. 80 parts Bis/GMA to 20 parts EBADMA | 29.5 +/− 3.6 lbs. |
| 3. 60 parts Bis/GMA to 40 parts EBADMA | 36.0 +/− 4.8 lbs. |
| 4. 40 parts Bis/GMA to 60 parts EBADMA | 34.6 +/− 5.9 lbs. |
| 5. 20 parts Bis/GMA to 80 parts EBADMA | 33.1 +/− 3.1 lbs. |
| 6. 0 parts Bis/GMA to 100 parts EBADMA | 28.4 +/− 3.5 lbs. |

The experimentation demonstrated that all the resin mixtures would possess adequate strength for orthodontic purposes. The strongest adhesive resulted from mixtures in the range of 60:40 to 20:80 Bis/GMA:EBADMA. The 90:10 Bis/GMA:EBADMA mixture was a bit gummy, and therefore the acceptable range is presently considered to be between 90:10 Bis/GMA:EBADMA and 0:100 Bis/GMA:EBADMA. The 60:40 ratio is the preferred ratio because it produces the highest strength, and was demonstrated to allow removal of the brackets without fracture of either the bracket or the tooth enamel.

The range of strength arising from the different mixtures allows an adhesive to be tailored to suit the orthodontic bracket being used. For example, it might be preferable to use one of the higher strength mixtures with a bracket with having a relatively small surface area.

In another experiment, the inventor compared stain resistance of the adhesive claimed herein against that of the common Bowen's resin. Light cured Bowen's resin was placed in cylindrical molds one-quarter inch in diameter by one-quarter inch long, and cured with a ten second exposure to a projector lamp. Ten samples were made. The adhesive claimed herein was also used to prepare ten cylindrical samples. All samples were then boiled for one hour in strong coffee. The samples were then removed from the coffee and rinsed thoroughly in tap water. The samples were then visually compared against one another and against samples that had not been boiled in coffee. Although both groups of samples contained only minor stain absorption, the Bowen's resin samples visually absorbed more of the coffee that did the samples comprised of the adhesive claimed herein.

In an alternative embodiment the adhesive is self-cured instead of light cured. In this embodiment, a bracket paste comprising the adhesive and a component of an initiator system is pre-dispensed onto brackets, and a primer comprising another component of the initiator system is applied to a tooth. When the bracket is attached to the tooth, the paste on the bracket contacts the primer on the tooth, and the components of the initiator system are activated to initiate curing of the adhesive.

There are numerous initiator systems which can utilized, including but not limited to those comprising an oxidizing agent and a reducing agent which generate free radicals to initiate the polymerization of dental resins within the bracket paste. In one example of such curing systems, the bracket paste comprises dibenzoyl peroxide and the primer comprises N,N(2-hydroxyethyl)-para-toluidine. In another example of such curing systems, the bracket paste comprises cumene hydroperoxide and the primer comprises $Cu^{+2}$ salts and acetylthiourea. The approximate formula of the preferred bracket paste is:

55 parts Bis/GMA
35 parts EBADMA
7 parts fumed silica
3 parts Dibenzoyl Peroxide
0.10 parts Butylated Hydroxytoluene.

Dibenzoyl Peroxide generates free radicals to initiate polymerization when mixed with the enamel primer. The chemical structure of Dibenzoyl Peroxide is

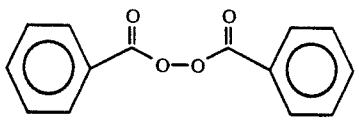

Butylated hydroxytoluene is added in order to prevent premature polymerization while in the package. It is available from numerous companies and is a common inhibitor added to dental resins. The chemical structure of Butylated Hydroxytoluene is

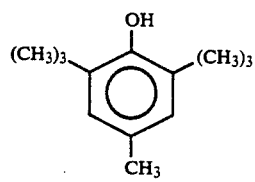

The bracket paste is made by first weighing out the appropriate amount of EBADMA. The butylated hydroxytoluene is added and stirring is performed until it completely dissolves. The Dibenzoyl Peroxide is then added and stirred until fully dissolved. The Bis/GMA is then added and stirred in until the consistency is uniform. The finely divided silica is then added and stirred thoroughly until uniform. The approximate formula of the preferred enamel primer is:

70 parts Bis/GMA
30 parts TEGDMA
3 parts N,N(2-Hydroxyethyl) p-Toluidine
7 parts finely divided silica TEGDMA is the acronym for triethylene glycol dimethylacrylate. It is used to dilute Bis/GMA down to an acceptable viscosity and to provide increased crosslinking to the primer. TEGDMA is available from Sartomer Resins as resin #205. The chemical structure of TEGDMA is

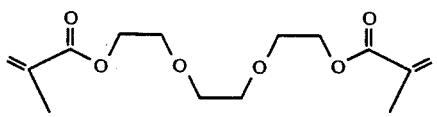

The enamel primer is made by first placing the appropriate amount of TEGDMA in a container. The N,N(2-hydroxyethyl) p-toluidine is then added to the TEGDMA and stirred until dissolved. The Bis/GMA is then added and stirred until the mixture is uniform. The finely divided silica is then added and stirred until the consistency is uniform.

Throughout the above discussion, the terms bracket and brackets are to be construed broadly to encompass all known and unknown brackets. This encompasses all shapes and sizes of dental brackets. This also encompasses brackets comprising any material or materials, including metals and ceramics, and any polymeric materials whether reinforced or not. The polymeric materials that are encompassed include without limitation polycarbonates, polyesters, polyurethanes, polysulfones, silicones, epoxy polymers, polyamides, polyimides and copolymers. Each of these polymers may be reinforced with any combination of materials, including without limitation metal, ceramic, carbon, graphite, aramid and polyester particles and fibers. The ceramic materials that are encompassed include without limitation polycrystalline and monocrystalline aluminum oxide, and also diamond, quartz, and other ceramic materials whether reinforced or not.

What is claimed is:

1. An improved dental bracket wherein the improvement comprises a fluid adhesive being pre-dispensed onto said bracket, said bracket inserted into a package and said adhesive in physical contact with said package.

2. The bracket of claim 1 wherein said adhesive retains satisfactory strength and workability while in storage for at least a year.

3. The bracket of claim 1 wherein said bracket is comprised of at least one of the following group of materials: ceramic, metal, polymer.

4. A packaging system comprising: a container having at least one compartment, a reservoir communicating with said at least one compartment, a dental bracket, and an adhesive in fluid contact with said reservoir and said bracket.

5. The packaging system of claim 4 wherein a portion of said at least one compartment is sized and dimensioned to serve as said reservoir for at least some of said adhesive.

6. The packaging system of claim 4 wherein said at least one compartment is opaque to visible light.

7. The packaging system of claim 4 wherein said adhesive comprises a mixture of Bis/GMA and EBADMA.

8. The packaging system of claim 4 wherein said adhesive retains satisfactory strength and workability while in storage for at least a year.

9. The packaging system of claim 4 wherein said bracket is comprised of at least one of the following group of materials: ceramic, metal, polymer.

10. A well containing a dental bracket having a bonding surface and a linkage surface, a free-flowing adhesive contacting said bonding surface and said well, a portion of said well mating with said bonding surface to form a seal which prevents said adhesive from contacting said linkage surface.

* * * * *